United States Patent [19]

Muramatsu et al.

[11] Patent Number: 4,465,851

[45] Date of Patent: Aug. 14, 1984

[54] GUANIDINOCYCLOHEXANECARBOXYLIC ACID DERIVATIVES

[75] Inventors: Mutsumi Muramatsu; Toshio Satoh, both of Tokushima; Hiroyasu Sekine, Kisai; Atsushi Tendo, Tokyo, all of Japan

[73] Assignee: Nippon Chemiphar Co., Ltd., Tokyo, Japan

[21] Appl. No.: 336,707

[22] Filed: Jan. 4, 1982

[30] Foreign Application Priority Data

Jan. 22, 1981 [JP]  Japan .................................. 56-7283
Jan. 22, 1981 [JP]  Japan .................................. 56-7284
Jan. 22, 1981 [JP]  Japan .................................. 56-7286
Jan. 29, 1981 [JP]  Japan .................................. 56-10831
Jan. 29, 1981 [JP]  Japan .................................. 56-10832

[51] Int. Cl.$^3$ .......................................... C07C 129/12
[52] U.S. Cl. .................................... 560/125; 546/174; 548/510; 260/465 D; 424/258; 424/274; 424/283; 424/304; 424/305; 549/401
[58] Field of Search ...................... 560/125; 546/174; 549/401; 548/509; 260/465 D

[56] References Cited

U.S. PATENT DOCUMENTS 3,699,149 10/1972 Yamamura ........................ 560/125
4,348,410 9/1982 Muramatsu ....................... 560/125

FOREIGN PATENT DOCUMENTS 49-62446  6/1974 Japan ................................. 560/125
51-40075 11/1976 Japan ................................. 560/125

*Primary Examiner*—Michael L. Shippen
*Attorney, Agent, or Firm*—Oblon, Fisher, Spivak, McClelland & Maier

[57] ABSTRACT

A compound having the formula

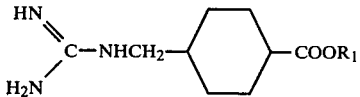

wherein $R_1$ represents an indanyl, indolyl, quinolyl or chromonyl group, the group of the formula

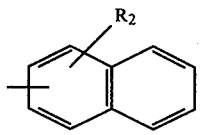

(in which $R_2$ represents a halogen atom or a nitro group), or the group of the formula

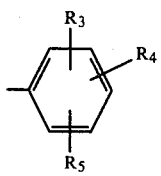

(in which $R_3$ represents a halogen atom, or an alkyl, nitro, cyano, acetamino, aminosulfonyl, benzoyl, phenoxy or trifluoromethyl group, $R_4$ represents a hydrogen or halogen atom, or an alkyl group, and $R_5$ represents a hydrogen or halogen atom, or an alkyl group), or a pharmaceutically acceptable salt thereof. The compound is obtained by reacting 4-guanidinomethylcyclohexanecarboxylic acid or a reactive derivative thereof with a compound of the formula $R_1$—OH wherein $R_1$ is the same as defined above, or a reactive derivative thereof.

2 Claims, No Drawings

GUANIDINOCYCLOHEXANECARBOXYLIC ACID DERIVATIVES

BACKGROUND OF THE INVENTION

1. Field of the Invention:

This invention relates to novel guanidinocyclohexanecarboxylic acid derivatives and a process for producing such derivatives.

2. Description of the Prior Art:

A. Okano et al have reported that 4-guanidinomethylcyclohexanecarboxylic acid exhibits slight antiplasmin effects [J. Med. Chem., Vol. 15, No. 3, 247(1972)]. M. Muramatsu and T. Satoh who are co-inventors of this invention, and other individuals have found that 4-guanidinomethylcyclohexanecarboxylic acid esters exhibit inhibitory effects on serine proteases and anti-ulcer effects (U.S. Ser. No. 186,849).

SUMMARY OF THE INVENTION

One object of the present invention is to provide novel guanidinocyclohexanecarboxylic acid derivatives which exhibit strong inhibitory effects on serine proteases and anti-allergic effects.

It is another object of the invention to provide a process for producing these novel guanidinocyclohexanecarboxylic acid derivatives.

These and other objects of the invention as hereinafter will become more readily apparent can be attained by the provision of compounds of the formula (I):

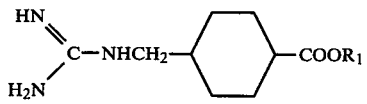

wherein $R_1$ represents an indanyl, indolyl, quinolyl or chromonyl group, the group of the formula (in which $R_2$ represents a halogen atom or a nitro group), or the group of the formula (in which $R_3$ represents a halogen atom, or an alkyl, nitro, cyano, acetamino, aminosulfonyl, benzoyl, phenoxy or trifluoromethyl group, $R_4$ represents a hydrogen or halogen atom, or an alkyl group, and $R_5$ represents a hydrogen or halogen atom, or an alkyl group). These derivatives and pharmaceutically acceptable salts thereof have been found to possess excellent inhibitory effects on serine proteases and anti-allergic effects. Particularly, compounds of the formula (II):

wherein $R_3$, $R_4$ and $R_5$ are the same as defined above, have been found to possess excellent anti-allergic effects.

DETAILED DESCRIPTION OF THE PREFERRED EMBODIMENTS

Ester residues of the present compounds defined as $R_1$ in the formula (I) may be indanyl, indolyl, guinolyl and chromonyl groups, the group of the formula (in which $R_2$ represents a halogen atom or a nitro group), or the group of the formula (in which $R_3$ represents a halogen atom, or an alkyl, nitro, cyano, acetamino, aminosulfonyl, benzoyl, phenoxy or trifluoromethyl group). Suitable groups of the formula include 4-chloro-α-naphthyl and 4-nitro-α-naphthyl groups. Suitable groups of the formula include chlorophenyl, bromophenyl, iodophenyl, methylphenyl, ethylphenyl, propylphenyl, butylphenyl, t-butylphenyl, nitrophenyl, cyanophenyl, acetaminophenyl, aminosulfonylphenyl, benzoylphenyl, phenoxyphenyl, trifluoromethylphenyl, 4-chloro-2-isopropyl-5-methylphenyl, 2-isopropyl-5-methylphenyl, 2,4-dichlorophenyl, 2,4,6-trichlorophenyl groups and the like.

Compounds of the formula (I) may be either the cis- or trans-isomer. Particularly preferable is the trans-isomer.

Pharmaceutically acceptable salts of the compounds are acid addition salts formed from hydrochloric acid, sulfuric acid, phosphoric acid, hydrobromic acid, acetic acid, lactic acid, maleic acid, fumaric acid, tartaric acid, citric acid, methanesulfonic acid, p-toluenesulfonic acid and like acids.

According to the invention, the compounds of the formula (I) are produced by reacting 4-guanidinomethylcyclohexanecarboxylic acid or a reactive derivative thereof with a compound of the formula (II):

$$R_1-OH \qquad (II)$$

wherein $R_1$ is the same as defined above, or a reactive derivative thereof.

Suitable reactive derivatives of 4-guanidinomethylcyclohexanecarboxylic acid include acid halides such for example as acid chloride, acid bromide and the like, and mixed anhydrides using ethylchloroformate. Suitable reactive derivatives of the compounds of the formula (II) include disulfite compounds such for example as bis-(4-chlorophenyl)sulfite and bis-(4-t-butylphenyl)sulfite.

The reaction of 4-guanidinomethylcyclohexanecarboxylic acid and the disulfite derivative of the compound of the formula (II) is carried out with stirring at room temperature for 1–20 hours. Suitable solvents which may be used include dimethylformamide, dimethylacetamide, pyridine and the like. The reaction of the reactive derivative of 4-guanidinomethylcyclohexanecarboxylic acid and the compound of the formula (II) is effected with stirring at a temperature of from room temperature to the boiling point of the solvent. Suitable solvents which may be used include dimethylformamide, dimethylacetamide, pyridine, dichloromethane, dichloroethane, chloroform, acetonitrile and the like. Use of an acid-binding agent such for example as triethylamine, dimethylaniline or pyridine is sometimes recommendable.

When 4-guanidinomethylcyclohexanecarboxylic acid is reacted directly without conversion to a reactive intermediate thereof, the reaction is preferably carried out in the presence of a condensing agent, for example, carbodiimide such as dicyclohexylcarbodiimide, or a Lewis acid such as phosphorusoxychloride or borontrifluoride. The reaction is accomplished using a solvent, for example, toluene, xylene or dimethylformamide, a solvent mentioned above, or a mixture thereof at a temperature of from room temperature to the boiling point of the solvent.

The thus obtained compounds of the formula (I) have some excellent pharmacological activity. That is, the present compounds exhibit excellent inhibitory effects on serine proteases such as trypsin, chymotrypsin, thrombin and urokinase. The compounds also exhibit excellent anti-allergic effects and have been found to strongly inhibit histamine release from mast cells by compound 48/80. Moreover, these compounds are significantly effective for preventing anaphylactic shock and experimental asthma in guinea pigs.

Inhibition of Various Serine Proteases

Inhibitory effects on the TAMe($N^\alpha$-tosyl-L-arginine methyl ester) hydrolytic activity of trypsin, plasmin, plasma kallikrein and thrombin were estimated by Hesterin's method modified by Roberts. Inhibition of the BAEe($N^\alpha$-benzoyl-L-arginine ethyl ester) hydrolytic activity of pancreas kallikrein was determined by Hesterin's method after incubation at 37° C. for 30 minutes in a 0.1M borate buffer, pH 8.0. Inhibitory effects on urokinase were determined by the chromotropic acid method after incubation of 60 iu of urokinase with 10 mM AGLMe(acetylglycyl-L-lysine methyl ester) at 37° C. for 30 minutes in a 0.06M phosphate buffer, pH 7.5, containing 0.09M NaCl. Inhibition of chymotrypsin was determined by Hesterin's method after incubation with 15 mM ATE ($N^\alpha$-acetyl-L-tyrosine ethyl ester) for 30 minutes at 37° C. in a 0.1M borate buffer, pH 8.0.

TABLE 1

Inhibition of Various Serine Proteases

Concentration for 50% inhibition ($IC_{50}$, M)

| Test compound | | Trypsin | Chymotrypsin | Plasmin | Pancreas kallikrein | Plasma kallikrein | Thrombin | Urokinase |
|---|---|---|---|---|---|---|---|---|
| Compound | 2 | $1.7 \times 10^{-4}$ | $9.7 \times 10^{-5}$ | $2.6 \times 10^{-4}$ | $6.2 \times 10^{-5}$ | $1.5 \times 10^{-4}$ | $2.5 \times 10^{-4}$ | $3.6 \times 10^{-5}$ |
| | 3 | | $7.0 \times 10^{-5}$ | | $3.2 \times 10^{-4}$ | | | $2.6 \times 10^{-4}$ |
| | 5 | $3.9 \times 10^{-4}$ | $1.2 \times 10^{-5}$ | | $9.0 \times 10^{-5}$ | $3.0 \times 10^{-4}$ | $1.6 \times 10^{-4}$ | $1.6 \times 10^{-4}$ |
| | 6 | $2.6 \times 10^{-4}$ | | | $1.5 \times 10^{-4}$ | | $1.8 \times 10^{-4}$ | |
| | 13 | | | $4.0 \times 10^{-4}$ | $4.0 \times 10^{-4}$ | | | $3.0 \times 10^{-5}$ |
| | 14 | $1.9 \times 10^{-4}$ | $1.0 \times 10^{-4}$ | $4.0 \times 10^{-4}$ | $1.3 \times 10^{-4}$ | | $2.4 \times 10^{-4}$ | |
| | 15 | $9.0 \times 10^{-5}$ | $2.8 \times 10^{-6}$ | | $2.5 \times 10^{-5}$ | $3.0 \times 10^{-4}$ | $9.5 \times 10^{-5}$ | $3.1 \times 10^{-5}$ |
| | 21 | | | $2.0 \times 10^{-4}$ | $3.0 \times 10^{-5}$ | | | $1.1 \times 10^{-4}$ |
| | 24 | | $6.0 \times 10^{-6}$ | | $2.0 \times 10^{-5}$ | | $2.3 \times 10^{-4}$ | $5.0 \times 10^{-5}$ |

Note:
The compound numerals denote the corresponding examples described hereinafter.

Effects on Histamine Release from Mast Cells Induced by Compound 48/80

Released histamine was determined by the fluorometric assay as follows: 1.5 ml of a mast cell suspension ($3.5 \times 10^5$/ml) was mixed with 1 ml of a physiological solution containing each test sample, and the resulting mixture was incubated for 7 minutes at 37° C., followed by addition of 1 ml of compound 48/80 (3.5 μg/ml). After incubation for 20 minutes at 37° C., the suspension was cooled to 4° C., and released histamine was determined as described by Shore et al. All samples examined were recognized to cause no disturbance in the fluorometric assay.

TABLE 2

Effects on Histamine Release from Mast Cells Induced by Compound 48/80

| Test compound | | Conc. of test compound | Inhibition of histamine release |
|---|---|---|---|
| Compound | 2 | 10 μg/ml | 46.7% |
| | 7 | 10 | 18.4 |
| | 14 | 10 | 38.8 |

TABLE 2-continued

Effects on Histamine Release from Mast Cells Induced by Compound 48/80

| Test compound | Conc. of test compound | Inhibition of histamine release |
|---|---|---|
| 23 | 10 | 12.7 |
| 28 | 10 | 60.9 |
| 29 | 10 | 20.6 |
| Compound A | 10 | 5.0 |
| DSCG | 10 | 10.0 |

Compound A:

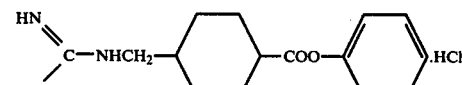

(Phenyl trans-4-guanidinomethylcyclohexanecarboxylate hydrochloride: Compound of U. S. Serial No. 186,849)
DSCG: Disodium cromoglycate It is known that DSCG has inhibitory effects on histamine release from mast cells [Life Sciences, Vol. 10, 805–812 (1971) and Internal Medicine, Vol. 42(6), 933 (1978)], and therefore, DSCG is used as an anti-allergic agent. However, the inhibitory effects of the present compounds on histamine release from mast cells are greater than those of DSCG.

Passive Cutaneous Anaphylaxis

Diluted anti-egg albumin (rat anti-egg albumin serum) with saline (0.05 ml) was subcutaneously injected into the back of a rat. 48 hours later, egg albumin and Evans' blue dissolved in saline (egg albumin 10 mg and Evans' blue 5 mg/ml) were intravenously injected into the rat in an amount of 2.5 ml/kg. 45 minutes later, the rat was killed, bled and skined, and the permeated area (mm$^2$) of the dye was measured. Test samples were administered per os 1 hour prior to antigen injection.

TABLE 3

Passive Cutaneous Anaphylaxis (Dilution ratio of antigen: × 32)

| Test compound | Dose | Inhibition |
|---|---|---|
| Compound 2 | 125 mg/kg, p.o. | 91.16% |

Schultz-Dale Reaction

Male guinea pigs were sensitized with bovine serum albumin by Freund's complete adjuvant method. After a lapse of 10 days, the animals were sensitized once more as described above. After two more weeks, an ileum of each sensitized guinea pig was removed and used for experiment. The ileum was equipped in a magnus tube containing each test sample, and 500 μg of bovine serum albumin was added. The contraction of the ileum was determined.

TABLE 4

Effects on Schlutz-Dale Reaction

| Test compound | Inhibition of contraction (%) Final conc. of compound | |
|---|---|---|
| | 50 μg/ml | 25 μg/ml |
| Compound 2 | 100 | 64.3 |
| 3 | 100 | 83.3 |
| 10 | 100 | 100 |
| 28 | 100 | 80 |
| Compound A | 0 | 0 |

Determination of Anti-acetylcholine and Anti-histamine Action

Anti-acetylcholine and anti-histamine effects of the present compounds were examined using guinea pigs ilea by the usual method.

Active Systemic Anaphylaxis in Mice

Egg albumin (10 mg) was mixed with 10 ml Bordetella pertusis vaccine (Takeda Chemical Industries, Ltd.), and the mixture was intraperitoneally injected into mice in an amount of 10 ml/kg. 22 days later, active systemic anaphylaxis was induced by intravenous injection of egg albumin dissolved in saline in an amount of 3 mg/10 ml/kg. A test sample suspended in 5% gum arabic was administered orally to the sensitized mice 1 hour prior to the antigen challenge. 24 hours after the antigen challenge, the number of survived mice was counted.

TABLE 5

Anti-acetylcholine and Anti-histamine Effects

| Test compound | Anti-acetylcholine effect inhibition of contraction (%) | | Anti-histamine effect inhibition of contraction (%) | |
|---|---|---|---|---|
| | Final conc. of compound | | | |
| | 50 μg/ml | 25 μg/ml | 50 μg/ml | 25 μg/ml |
| Compound 2 | 100 | 96 | 96.5 | 82 |
| 3 | 100 | 100 | 100 | 98 |
| 10 | 100 | 89.8 | 100 | 100 |
| 28 | 76 | 68 | 100 | 99.7 |
| 29 | 80 | 52 | — | — |
| Compound A | — | — | 100 | 100 |
| DSCG | — | — | 0 | 0 |

TABLE 6

Active Systemic Anaphylaxis in Mice

| | Survival after 24 hr. (5 mice) | | |
|---|---|---|---|
| Compound | 500 mg/kg | 250 mg/kg | 100 mg/kg |
| Compound 2 | 4 | 2 | 2 |

All the animals (5 mice) of a control group died.

Experimental Asthma in Sensitized Guinea Pigs

Hartley male guinea pigs each weighing 300 to 350 g were passively sensitized by intravenous injection with rabbit anti-egg albumin serum (0.5 ml/kg). 24 hours after passive sensitization, the guinea pigs were placed in a chamber for an inhalation test and then subjected to continuous spraying for 900 seconds with a mist of a 2% egg albumin solution. A test sample suspended in 5% gum arabic was orally administered 1 hour prior to the antigen challenge. The preconvulsion time was measured.

The evaluation was also performed in the experimental asthma with actively sensitized guinea pigs as follows: Hartley male guinea pigs each weighing 300 to 350 g were sensitized (by subcutaneous injection into the inguinal region) with an egg albumin solution (1 mg/ml) emulsified with an equal volume of Freund's complete adjuvant (5 mg/kg of body weight). Ten days later, the emulsion was injected subcutaneously into the axilla. On the 26th day after the first sensitization, the animals were subjected to the experiments which were conducted in the same manner as in the passively sensitized animals. The results obtained are shown in Table 7 and Table 8.

TABLE 7

Prevention of Experimental Asthma with Passively Sensitized Guinea Pigs

| Test compound | Time to fall down (sec.) |
|---|---|
| Control (12 animals) | <u>110</u>, <u>127</u>, 1 3 5, 1 6 2, <u>116</u>, <u>139</u>, <u>153</u>, |
| | <u>172</u>, <u>127</u>, <u>136</u>, 1 9 4, >900 |
| Compound 2 | <u>58</u>, 1 4 2, 1 9 1, >900, >900, >900, |
| (500 mg/kg) (10 animals) | >900, >900, >900, >900 |

—— Died within 15 minutes
- - - Recovered within 15 minutes after falling down

TABLE 8

Prevention of Experimental Asthma with Actively Sensitized Guinea Pigs

| Test compound | Time to fall down (sec.) |
|---|---|
| Control | <u>271</u>, <u>299</u>, <u>349</u>, <u>277</u>, <u>230</u>, 412 |
| Compound 2 | |
| 500 mg/kg | 768, >900, >900, >900, >900 |
| 250 | 632, >900, >900, >900, >900 |
| 125 | 699, >900, >900, >900, >900 |

—— Died within 15 minutes

The toxicity of a typical compound of the present compounds is described below.

Acute Toxicity

Normal ICR strain mice (female: 22 g, male: 24 g) or Wister strain rats (female: 90 g, male: 95 g) were used. A test compound was orally given using a gastric sonde. The animals were observed for 7 days. The $LD_{50}$ values were calculated by the Litchfield-Wilcoxon method. The results obtained are shown in Table 9.

TABLE 9

| | Acute Toxicity $LD_{50}$ (mg/kg) | | | |
|---|---|---|---|---|
| | Mouse | | Rat | |
| Test compound | Female | Male | Female | Male |
| Compound 2 | 7300 | 5400 | 10,800 | 11,000 |

The compounds of the invention are satisfactorily administered by both oral and parenteral routes. Needless to mention, the oral mode of administration is the most preferable and can be made in the form of a capsule, a tablet, a powder or a granule. In the dosage form, the active compounds are admixed with at least one inert diluent such as lactose, corn starch or crystalline cellulose; a lubricant such as magnesium stearate; a binder such as hydroxy propylcellulose; a coloring material; perfumery; a sweetening agent; and the like.

The dosage of the compounds according to the invention in various compositions actually utilized may be varied. However, it is necessary that the amount of the compounds be such that two suitable dosage forms are attained. Any selected dosage depends upon the desired therapeutic effect, the administration route and the treatment duration. Such dosage lies, in general, in a range from 30 to 900 mg/day.

This invention is illustrated in further detail with reference to certain specific Examples which are presented herein for purposes of illustration only and are not to be construed as limiting to the invention.

EXAMPLE 1

2'-Methylphenyl trans-4-guanidinomethylcyclohexanecarboxylate hydrochloride

A mixture of 5.9 g of trans-4-guanidinomethylcyclohexanecarboxylic acid hydrochloride, 3.24 g of o-cresol and 6.2 g of dicyclohexylcarbodiimide was suspended in 100 ml of dry pyridine, and the suspension was reacted at room temperature for 14 days. After completion of the reaction, any insoluble materials were removed by filtration, and the filtrate was evaporated to dryness. To the residue was added ether, and the mixture was decanted to wash twice and then was washed twice with toluene. After removal of toluene, the crystals obtained were recrystalized from isopropanol to obtain 2.64 g (yield: 32%) of 2'-methylphenyl trans-4-guanidinomethylcyclohexanecarboxylate hydrochloride as colorless crystals having a melting point of 157°–159° C.

IR $\nu_{max}^{KBr}$ cm$^{-1}$: 1748 (C=O).

EXAMPLE 2

4'-t-Butylphenyl trans-4-guanidinomethylcyclohexanecarboxylate hydrochloride

A mixture of 9.4 g of trans-4-guanidinomethylcyclohexanecarboxylic acid, 7.2 g of p-t-butylphenol and 10.0 g of dicyclohexylcarbodiimide was suspended in a solution of 61 ml of dry pyridine and ml of dry dimethylformamide, and the suspension was stirred at room temperature for 24 hours. The solvent was removed under reduced pressure. To the residue was added 240 ml of 0.1N hydrochloric acid, and the mixture was stirred at room temperature for 1 hour. Any insoluble materials were removed by filtration and washed with ethyl acetate. The filtrate and the washing were combined and stirred to obtain an aqueous layer. After filtration of the aqueous layer, the filtrate was evaporated under reduced pressure, and the residue was cooled to give crystals. The crystals were washed with ether and recrystalized from ethanol-ether to obtain 10.3 g (yield: 70%) of 4'-t-butylphenyl trans-4-guanidinomethylcyclohexanecarboxylate hydrochloride as colorless crystals having a melting point of 189°–196° C. The crystals were recrystalized again from ethanol-ether to obtain colorless crystals having a melting point of 208°–210° C.

IR $\nu_{max}^{KBr}$ cm$^{-1}$: 1750 (C=O).

NMR(CD$_3$OD) $\delta$: 0.60–2.80 (10 H, m, cyclohexane protons), 1.38 (9H, s, —C(CH$_3$)$_3$), 3.20 (2H, d, J=8 Hz, —C$\underline{H}_2$—N), 7.20–7.90 (4H, m, aromatic protons).

EXAMPLE 3

4'-Methylphenyl trans-4-guanidinomethylcyclohexanecarboxylate hydrochloride

A mixture of 8.9 g of bis(p-methylphenyl)sulfite obtained from p-methylphenol and thionylchloride, 2.0 g of trans-4-guanidinomethylcyclohexanecarboxylic acid hydrochloride, 18 ml of dry dimethylformamide and 9 ml of dry pyridine was stirred at room temperature for 16 hours. After completion of the reaction, the solvent was removed under reduced pressure. To the residue was added diethyl ether to give crystals. The crystals were washed with diethyl ether and then with ethyl acetate, and recrystalized from methanol-diethyl ether to obtain 1.93 g (yield: 69.9%) of 4'-methylphenyl trans-4-guanidinomethylcyclohexanecarboxylate hydrochloride as colorless crystals having a melting point of 151°–153° C.

IR $\nu_{max}^{KBr}$ cm$^{-1}$: 1639, 1663, 1742.

NMR(CD$_3$OD) δ: 0.78–2.55 (10H, m, cyclohexane protons), 2.29 (3H, s, C$\underline{H}_3$), 3.05 (2H, d, N—C$\underline{H}_2$—), 6.72–7.46 (4H, m, aromatic protons).

EXAMPLE 4

4'-Ethylphenyl trans-4-guanidinomethylcyclohexanecarboxylate hydrochloride

A mixture of 2.35 g of trans-4-guanidinomethylcyclohexanecarboxylic acid hydrochloride, 2.47 g of dicyclohexylcarbodiimide and 1.46 g of p-ethylphenol was added to a mixture of 30 ml of dry pyridine and 10 ml of dry dicyclohexylcarbodiimide, and the resulting mixture was stirred at 30° C. for 2 days. After being filtered, the precipitate was washed with 10 ml of pyridine. The filtrate and the washing were combined, and the solvent was evaporated. The residue was washed with ether and then with ethyl acetate, and extracted with 20 ml of acetone. To the acetone layer was added ether to give crystals. The crystals were recrystalized from methanol-ether to obtain 410 mg of 4'-ethylphenyl trans-4-guanidinomethylcyclohexanecarboxylate hydrochloride as colorless crystals having a melting point of 137°–139° C.

IR $\nu_{max}^{KBr}$ cm$^{-1}$: 1750.

EXAMPLE 5

2'-Chlorophenyl trans-4-guanidinomethylcyclohexanecarboxylate hydrochloride

A mixture of 1.18 g of trans-4-guanidinomethylcyclohexanecarboxylic acid hydrochloride, 1.24 g of dicyclohexylcarbodiimide, 0.77 g of o-chlorophenol and 20 ml of dry pyridine was stirred at room temperature for 4 days. The precipitate was removed from the reaction mixture by filtration. The filtrate was evaporated, and to the residue was added 10 ml of dioxane to give crystals. The crystals were recrystallized from iso-propanol to obtain 1.27 g (yield: 70%) of 2'-chlorophenyl trans-4-guanidinomethylcyclohexanecarboxylate hydrochloride as colorless crystals having a melting point of 157°–158° C.

IR $\nu_{max}^{KBr}$ cm$^{-1}$: 1723 (C=O).

EXAMPLE 6

4'-Bromophenyl trans-4-guanidinomethylcyclohexanecarboxylate hydrochloride

A mixture of 1.18 g of trans-4-guanidinomethylcyclohexanecarboxylic acid hydrochloride, 1.24 g of dicyclohexylcarbodiimide, 1.04 g of 4-bromophenol and 20 ml of dry pyridine was stirred at room temperature for 2 days. The precipitate was removed from the reaction mixture by filtration, and the filtrate was evaporated. To the residue was added 10 ml of acetone to give crystals. The crystals were recrystalized from iso-propanol to obtain 1.06 g (yield: 52%) of 4'-bromophenyl trans-4-guanidinomethylcyclohexanecarboxylate hydrochloride as colorless crystals having a melting point of 165°–166° C.

IR $\nu_{max}^{KBr}$ cm$^{-1}$: 1735 (C=O).

EXAMPLE 7

4'-Iodophenyl trans-4-guanidinomethylcyclohexanecarboxylate hydrochloride

A mixture of 10.7 g of trans-4-guanidinomethylcyclohexanecarboxylic acid hydrochloride, 10 g of p-iodophenol, 9.4 g of dicyclohexylcarbodiimide and 100 ml of dry pyridine was stirred at room temperature for 17 hours. After removal of any insoluble materials by filtration, pyridine was evaporated under reduced pressure. To the residue was added 300 ml of 0.1N hydrochloric acid to give white substances which were washed with warm ethyl acetate and dissolved in methanol. After removal of any insoluble materials by filtration with cooling, ether was added to the methanol solution to obtain 10 g (yield: 50.3%) of 4'-iodophenyl trans-4-guanidinomethylcyclohexanecarboxylate hydrochloride as colorless crystals having a melting point of 195°–197° C.

IR $\nu_{max}^{KBr}$ cm$^{-1}$: 1740 (C=O).

NMR (CD$_3$OD, CDCl$_3$) δ: 0.96–2.70 (10H, m, cyclohexane protons), 3.06 (2H, d, J=7 Hz, —C$\underline{H}_2$—), 6.80–7.80 (4H, m, aromatic protons).

EXAMPLE 8

2',4',6'-Trichlorophenyl trans-4-guanidinomethylcyclohexanecarboxylate hydrochloride A mixture of 5 g of trans-4-guanidinomethylcyclohexanecarboxylic acid hydrochloride, 4.2 g of 2,4,6-trichlorophenol, 4.4 g of dicyclohexylcarbodiimide and 50 ml of dry pyridine was stirred at room temperature for 17 hours. After removal of any insoluble materials by filtration, pyridine was evaporated under reduced pressure. To the oil substance obtained was added ethyl acetate to give pale yellow substances which were dissolved in warm chloroform. After removal of any insoluble materials by filtration, the solution was cooled to give colorless powders which were washed with cold chloroform and then with ether to obtain 4 g (yield: 45.5%) of 2',4',6'-trichlorophenyl trans-4-guanidinomethylcyclohexanecarboxylate hydrochloride as colorless powders having a melting point of 151°–155° C.

IR $\nu_{max}^{KBr}$ cm$^{-1}$: 1760 (C=O).

(NMR(CD$_3$OD) δ: 1.00–2.90 (10H, m, cyclohexane protons), 3.10 (2H, d, J=7 Hz, —C$\underline{H}_2$—), 7.52 (2H, s, aromatic protons).

EXAMPLE 9

2',4'-Dichlorophenyl trans-4-guanidinomethylcyclohexanecarboxylate hydrochloride 1 g of bis(2,4-dichlorophenyl)sulfite and 5 ml of dry pyridine were added to a mixture of 3 g of trans-4-guanidinomethylcyclohexanecarboxylic acid and 15 ml of dry dimethylformamide with cooling in a water bath, and the mixture was stirred for 2 hours. The solvent was removed, and the residue was washed with ether to give a gummy substance which was dissolved in 30 ml of methanol. The solution was treated with charcoal, and the resulting solution was evaporated to dryness under reduced pressure. Ether and 20 ml of acetone were added to the residue, and the mixture was stirred to crystalize. The crystals were obtained by filtration and washed with a small amount of acetone and then with diethyl ether to obtain 2.7 g (yield: 56%) of 2',4'-dichlorophenyl trans-4-guanidinomethylcyclohexanecarboxylate hydrochloride as colorless powders having a melting point of 133°-138° C.

IR $\nu_{max}^{KBr}$ cm$^{-1}$: 1760.

NMR(CD$_3$OD) δ: 0.84-2.80 (10H, m, cyclohexane protons), 2.96-3.16 (2H, m, —C$\underline{H}_2$—N), 7.00-7.52 (3H, m, aromatic protons).

EXAMPLE 10

4'-Chlorophenyl trans-4-guanidinomethylcyclohexanecarboxylate hydrochloride A mixture of 2.0 g of trans-4-guanidinomethylcyclohexanecarboxylic acid hydrochloride and 8.5 g of bis(p-chlorophenyl)sulfite obtained from p-chlorophenol and thionyl chloride was stirred at room temperature for 1 hour in a solution of 18 ml of dry dimethylformamide and 9 ml of dry pyridine. The solvent was removed under reduced pressure, and the residue was washed with diethyl ether to give crystals. The crystals were washed with diethyl ether and then with ethyl acetate, and thereafter recrystalized from methanol-diethyl ether to obtain 1.77 g (yield: 60.2%) of 4'-chlorophenyl trans-4-guanidinomethylcyclohexanecarboxylate hydrochloride as colorless crystals having a melting point of 163°-165° C.

IR $\nu_{max}^{KBr}$ cm$^{-1}$: 1747.

NMR(CD$_3$OD) δ: 0.81-2.88 (10H, m, cyclohexane protons), 3.26 (2H, d, N—C$\underline{H}_2$—), 7.28-7.99 (4H, m, aromatic protons).

EXAMPLE 11

4'-Chlorophenyl trans-4-guanidinomethylcyclohexanecarboxylate hydrochloride A mixture of 2.35 g of trans-4-guanidinomethylcyclohexanecarboxylic acid hydrochloride, 2.47 g of dicyclohexylcarbodiimide, 1.54 g of p-chlorophenol and 50 ml of dry pyridine was stirred at 30° C. for 3 days. After being filtrated, the precipitate was washed with 10 ml of pyridine. The filtrate and the washing were combined and evaporated. 5 ml of cold water was added to the residue, and the precipitate was removed by filtration. The filtrate was evaporated under reduced pressure, and the residue was washed with ether and then with ethyl acetate. Warm acetone was added to the residue, and the solution was cooled to obtain crystals. The crystals were recrystalized from methanol-ether to obtain 4'-chlorophenyl trans-4-guanidinomethylcylohexanecarboxylate hydrochloride.

EXAMPLE 12

2',4'-Dimethylphenyl trans-4-guanidinomethylcyclohexanecarboxylate hydrochloride A mixture of 5.9 g of trans-4-guanidinomethylcyclohexanecarboxylic acid hydrochloride, 6.18 g of dicyclohexylcarbodiimide, 3.66 g of 2,4-dimethylphenol and 100 ml of dry pyridine was stirred at 30° C. for 4 days. After removal of any insoluble materials by filtration, the filtrate was concentrated under reduced pressure. The residue was washed with ether and then with ethyl acetate. Benzene was added to the resulting residue, and the solution was stirred to crystalize. The crystals were recrystalized from isopropanol-ethyl acetate to obtain 6.22 g (yield: 73%) of 2',4'-dimethylphenyl trans-4-guanidinomethylcyclohexanecarboxylate hydrochloride as colorless crystals having a melting point of 151°-153° C.

IR $\nu_{max}^{KBr}$ cm$^{-1}$: 1745 (C=O).

EXAMPLE 13

2'-iso-Propyl-5'-methylphenyl trans-4-guanidinomethylcyclohexanecarboxylate hydrochloride A mixture of 10.0 g of trans-4-guanidinomethylcyclohexanecarboxylic acid hydrochloride, 6.4 g of thymol, 8.75 g of dicyclohexylcarbodiimide and 100 ml of dry pyridine was stirred at room temperature for 36 hours. After removal of any insoluble materials, the filtrate was concentrated under reduced pressure. 200 ml of 0.1N hydrochloric acid was added to the residue with cooling, and the mixture was stirred at room temperature for 12 hours. After removal of the precipitate by filtration, a small amount of water was added to the filtrate, and the mixture was allowed to stand to give white crystals. The crystals were dissolved in methanol, and the precipitate was removed by filtration. The filtrate was evaporated, and water was added to the residue to give white crystals which were recrystalized from water-methanol to obtain 6.0 g of 2'-iso-propyl-5'-methylphenyl trans-4-guanidinomethylcyclohexanecarboxylate hydrochloride as colorless crystals having a melting point of 158°-160° C.

IR $\nu_{max}^{KBr}$ cm$^{-1}$: 1730 (C=O).

NMR(CD$_3$OD) δ: 1.15 (6H, d, CH(C$\underline{H}_3$)$_2$), 0.91-2.36 (10H, m, cyclohexane protons), 2.27 (3$\underline{H}$, s, C$\underline{H}_3$), 2.95 (1H, m, C$\underline{H}$(CH$_3$)$_2$).

EXAMPLE 14

2'-iso-Propyl-4'-chloro-5'-methylphenyl trans-4-guanidinomethylcyclohexanecarboxylate hydrochloride A mixture of 10 g of trans-4-guanidinomethylcyclohexanecarboxylic acid hydrochloride, 7.83 g of 2-iso-propyl-4-chloro-5-methyl phenol and 8.75 g of dicyclohexylcarbodiimide was suspended in 100 ml of dry pyridine, and the suspension was stirred at room temperature for 14 hours. After removal of any insoluble materials, the precipitate was washed with pyridine. The filtrate and the washing were combined, and the solvent was removed. 200 ml of 0.1N hydrochloric acid was added to the residue, and the mixture was stirred for 30 minutes to give crystals. The crystals were washed with water, ethyl acetate, benzene and then ether. The crystals were dissolved in isopropanol, and any insoluble materials were removed by filtration. The filtrate was evaporated, and to this residue was added isopropyl ether. This solution was allowed to stand at 3° C. to give crystals which were recrystalized from isopropanol-isopropyl ether to obtain 5 g of 2-iso-propyl-4'-chloro-5'-methylphenyl trans-4-guanidinomethylcyclohexanecarboxylate hydrochloride as colorless crystals having a melting point of 185°-187° C.

IR $\nu_{max}^{KBr}$ cm$^{-1}$: 1735 (C=O).

NMR(CD$_3$OD) δ: 1.10 (3H, d, J=7.2 Hz CHC$\underline{H}_3$), 2.26 (3H, s, C$\underline{H}_3$), 3.03 (2H, d, J—6 Hz, C$\underline{H}_2$N), 6.97 (1H, s, aromatic proton), 7.36 (1H, s, aromatic proton).

EXAMPLE 15

4'-Nitrophenyl trans-4-guanidinomethylcyclohexanecarboxylate hydrochloride

A mixture of 5.0 g of trans-4-guanidinomethylcyclohexanecarboxylic acid hydrochloride, 6.18 g of dicyclohexylcarbodiimide and 6.95 g of p-nitrophenol was suspended in 100 ml of dry pyridine, and the suspension was stirred at room temperature for 40 hours. After removal of any insoluble materials, the filtrate was evaporated. Acetone was added to the residue, and any insoluble materials were removed by filtration. Acetone was removed, and ethyl acetate was added to the residue to deposit crystals. The crystals were recrystalized from isopropanol to obtain 1.9 g (yield: 25%) of 4'-nitrophenyl trans-4-guanidinomethylcyclohexanecarboxylate hydrochloride as colorless crystals having a melting point of about 155° C.

IR $\nu_{max}^{KBr}$ cm$^{-1}$: 1760 (C=O).

EXAMPLE 16

4'-Acetaminophenyl trans-4-guanidinomethylcyclohexanecarboxylate hydrochloride A mixture of 1.17 g of trans-4-guanidinomethylcyclohexanecarboxylic acid hydrochloride, 1.13 g of dicyclohexylcarbodidimide and 0.83 g of p-acetaminophenol was suspended in 30 ml of dry pyridine, and the resulting suspension was stirred at 30° C. for 15 days. The crystals deposited were obtained by filtration and suspended in about 10 ml of cold water. After removal of any insoluble materials, the filtrate was evaporated to give colorless crystals. The crystals were recrystalized from isopropanol-ethyl acetate to obtain 495 mg (yield: 27.2%) of 4'-acetaminophenyl trans-4-guanidinomethylcyclohexanecarboxylate hydrochloride as colorless crystals having a melting point of 223°-224° C.

IR $\nu_{max}^{KBr\ cm-1}$: 1755 (C=O).

EXAMPLE 17

4'-Benzoylphenyl trans-4-guanidinomethylcyclohexanecarboxylate hydrochloride A mixture of 1.18 g of trans-4-guanidinomethylcyclohexanecarboxylic acid hydrochloride, 1.24 g of dicyclohexylcarbodiimide and 1.18 g of 4-hydroxybenzophenone was suspended in 20 ml of dry pyridine, and the suspension was stirred at room temperature for 9 days. After removal of any insoluble materials, the filtrate was evaporated. The residue was washed with benzene and dried, and acetone was added to the residue to deposit crystals. The crystals obtained were recrystalized from isopropanol to obtain 442 mg (yield: 21%) of 4'-benzoylphenyl trans-4-guanidinomethylcyclohexanecarboxylate hydrochloride as colorless crystals having a melting point of 199°-200° C.

IR $\nu_{max}^{KBr\ cm-1}$: 1755 (C=O).

EXAMPLE 18

4'-Aminosulfonylphenyl trans-4-guanidinomethylcyclohexanecarboxylate hydrochloride A mixture of 5.90 g of trans-4-guanidinomethylcyclohexanecarboxylic acid hydrochloride, 6.18 g of dicyclohexylcarbodiimide and 5.19 g of p-phenol sulfonamide was suspended in 100 ml of dry pyridine, and the suspension was stirred at 30° C. for 12 days. After removal of any insoluble materials, the filtrate was evaporated. Ethyl acetate was added to the residue, and the mixture was stirred and allowed to stand. To the residue obtained by decantation was added ethyl acetate. The crystals were recrystalized from ethanol-ethyl acetate to obtain 6.4 g (yield: 65%) of 4'-aminosulfonylphenyl trans-4-guanidinomethylcyclohexanecarboxylate hydrochloride as pale yellowish brown powders having a melting point of 194°-196° C.

EXAMPLE 19

2'-Phenoxyphenyl trans-4-guanidinomethylcyclohexanecarboxylate hydrochloride (a) A mixture of 10 g of o-phenoxyanisol, 80 ml of hydroiodic acid (52%), 80 ml of acetic acid and 40 ml of acetic anhydride was refluxed for 1.5 hours. After being cooled, the reaction mixture was poured into ice-water to deposit a precipitate. The precipitate was dissolved in ether, and the solution was washed with an aqueous saturated sodium chloride solution, an aqueous saturated thiosulfuric acid aqueous solution and then an aqueous saturated sodium chloride solution. This ether solution was dried over anhydrous sodium sulfate, and the solvent was removed to give yellow solids. The solids were dissolved in acetic acid and stirred. The mixture was poured into cold water to deposit crystals. The crystals were washed with water and then with n-hexane, and dried at 80° C. under reduced pressure to obtain 7.8 g of o-phenoxyphenol as slightly yellow powders.

NMR(CDCl$_3$) δ: 5.50 (1H, broad s, OH), 6.60–7.40 (9H, m, aromatic protons).

(b) A mixture of 7.5 g of trans-4-guanidinomethylcyclohexanecarboxylic acid hydrochloride, 6 g of o-phenoxyphenol, 6.5 g of dicyclohexylcarbodiimide and 80 ml of dry pyridine was stirred at room temperature for 24 hours. After removal of any insoluble materials, the solvent was removed under reduced pressure. Water was added to the residue, and any insoluble materials were removed by filtration, and the filtrate was evaporated under reduced pressure. The residue was washed with benzene and then with dry benzene. After being dried, the residue was washed twice with dry ether to obtain 9 g (yield: 69.2%) of 2'-phenoxyphenyl trans-4-guanidinomethylcyclohexanecarboxylate hydrochloride as hygroscopic, slightly yellow powders having a melting point of 73°-75° C.

IR $\nu_{max}^{KBr}$ cm$^{-1}$: 1755 (C=O).

NMR(CD$_3$OD) δ: 1.70–2.56 (10H, m, cyclohexane protons), 3.00 (2H, d, J=8 Hz, —CH$_2$), 6.80–7.40 (9H, m, aromatic protons).

EXAMPLE 20

3'-Trifluoromethylphenyl trans-4-guanidinomethylcyclohexanecarboxylate hydrochloride A mixture of 10.0 g of trans-4-guanidinomethylcyclohexanecarboxylic acid hydrochloride, 6.9 g of m-trifluoromethylphenol and 8.75 g of dicyclohexylcarbodiimide was suspended in 100 ml of dry pyridine, and the suspension was stirred at room temperature for 18 hours. After removal of any insoluble materials, the filtrate was evaporated under reduced pressure to give pale yellow crystals. 200 ml of 0.1N hydrochloric acid was added to the crystals, and the mixture was stirred for 1 hour to give crystals. The crystals were washed with water and recrystalized from ethyl acetate-ether to obtain 9.6 g (yield: 59.7%) of 3'-trifluoromethylphenyl trans-4-guanidinomethylcyclohexanecarboxylate hydrochloride as needles having a melting point of 88°–91° C.

IR $\nu_{max}^{KBr}$ cm$^{-1}$: 1742 (C=O).

NMR(CD$_3$OD) δ: 0.98–2.16 (10H, m, cyclohexane protons), 3.11 (2H, d, C$\underline{H}_2$N), 7.34–7.83 (4H, m, aromatic protons).

EXAMPLE 21

2'-Cyanophenyl trans-4-guanidinomethylcyclohexanecarboxylate hydrochloride

A mixture of 9.88 g of trans-4-guanidinomethylcyclohexanecarboxylic acid hydrochloride, 5 g of o-cyanophenol and 8.64 g of dicyclohexylcarbodiimide was suspended in 100 ml of dry pyridine, and the suspension was stirred at room temperature for 66 hours. Any insoluble materials were removed by filtration and then washed with pyridine. The filtrate and the washing were combined and evaporated. The residue was washed with ethyl acetate and then dissolved in 30 ml of ethanol. After removal of any insoluble materials, 10 ml of water was added to the filtrate. The mixture was cooled to obtain 9.82 g of 2'-cyanophenyl trans-4-guanidinomethylcyclohexanecarboxylate hydrochloride as colorless needles having a melting point of 102°–105° C.

IR $\nu_{max}^{nujol}$ cm$^{-1}$: 2250 (CN), 1760 (C=O).

NMR(CD$_3$OD) δ: 0.9–2.8 (10H, m, cyclohexane protons), 3.01 (2H, d, J=6 Hz, C$\underline{H}_2$N), 7.14–7.65 (4H, m, aromatic protons).

EXAMPLE 22

4'-Cyanophenyl trans-4-guanidinomethylcyclohexanecarboxylate hydrochloride

A mixture of 9.88 g of trans-4-guanidinomethylcyclohexanecarboxylic acid hydrochloride, 5 g of p-cyanophenol and 8.64 g of dicyclohexylcarbodiimide was suspended in 100 ml of dry pyridine, and the suspension was stirred at room temperature for 18 hours. After removal of any insoluble materials, the filtrate was washed with pyridine and then with ether. 100 ml of methanol was added to the crystals obtained, and the mixture was stirred for 15 minutes. Any insoluble materials were removed by filtration, and the filtrate was cooled to −50° C. to deposit insoluble materials which were removed by filtration. The filtrate was evaporated to obtain 7.7 g of 4'-cyanophenyl trans-4-guanidinomethylcyclohexanecarboxylate hydrochloride as colorless crystals having a melting point of 182°–186° C.

IR $\nu_{max}^{KBr}$ cm$^{-1}$: 2225 (CN), 1735 (C=O).

NMR(CD$_3$OD) δ: 0.9–2.8 (10H, m, cyclohexane protons), 3.08 (2H, d, J=6.4 Hz, C$\underline{H}_2$N), 7.30 and 7.79 (each 2H, each d, J=8 Hz, aromatic protons).

EXAMPLE 23

5'-Indanyl trans-4-guanidinomethylcyclohexanecarboxylate hydrochloride

A mixture of 5.6 g of trans-4-guanidinomethylcyclohexanecarboxylic acid hydrochloride, 3.18 g of 5-hydroxyindane and 5.9 g of dicyclohexylcarbodiimide was dissolved in a solution of 30 ml of dry pyridine and 35 ml of dry dimethylformamide, and the solution was allowed to stand overnight at room temperature. After removal of any insoluble materials, the filtrate was evaporated under reduced pressure. 50 ml of 0.1N hydrochloric acid was added to the residue to give crystals which were recrystalized from isopropanol to obtain 4.39 g (yield: 53%) of 5'-indanyl trans-4-guanidinomethylcyclohexanecarboxylate hydrochloride having a melting point of 157°–159° C.

IR $\nu_{max}^{KBr}$ cm$^{-1}$: 1760 (C=O).

EXAMPLE 24

7'-(2'-Oxochromenyl)trans-4-guanidinomethylcyclohexanecarboxylate hydrochloride

A mixture of 5.6 g of trans-4-guanidinomethylcyclohexanecarboxylic acid hydrochloride, 3.84 g of 7-hydroxycoumarin and 5.9 g of dicyclohexylcarbodiimide was dissolved in a solution of 35 ml of dry dimethylformamide and 30 ml of dry pyridine, and the solution was allowed to stand overnight at room temperature. After removal of any insoluble materials, the filtrate was evaporated under reduced pressure. 50 ml of water was added to the residue to give crystals which were recrystalized from isopropanolmethanol to obtain 6.04 g (yield: 72%) of 7'-(2'-oxochromenyl)-trans-4-guanidinomethylcyclohexanecarboxylate hydrochloride having a melting point of 179°–181° C.

IR $\nu_{max}^{KBr}$ cm$^{-1}$: 1740, 1762 (C=O).

EXAMPLE 25

4'-Indolyl trans-4-guanidinomethylcyclohexanecarboxylate hydrochloride

A mixture of 5.2 g of trans-4-guanidinomethylcyclohexanecarboxylic acid hydrochloride, 2.93 g of 4-hydroxyindole and 5.0 g of dicyclohexylcarbodiimide was dissolved in a solution of 25 ml of dry pyridine and 25 ml of dry dimethylformamide, and the solution was allowed to stand overnight at room temperature. After removal of any insoluble materials, the filtrate was evaporated under reduced pressure. 20 ml of isopropanol and 1 ml of water were added to the residue, and the mixture was allowed to stand for 1–2 hours. Insoluble materials were removed by filtration, and the filtrate was evaporated under reduced pressure. Water was added to the residue to give crystals which were recrystalized from ethanol to obtain 5.22 g (yield: 67.5%) of 4'-indolyl trans-4-guanidinomethylcyclohexanecarboxylate hydrochloride having a melting point of 182°–183° C.

IR $\nu_{max}^{KBr}$ cm$^{-1}$: 1740 (C=O).

EXAMPLE 26

8'-Quinolyl trans-4-guanidinomethylcyclohexanecarboxylate hydrochloride

A mixture of 5.2 g of trans-4-guanidinomethylcyclohexanecarboxylic acid hydrochloride, 3.19 g of 8-hydroxyquinoline and 5.0 g of dicyclohexylcarbodiimide was dissolved in a solution of 30 ml of dry pyridine and 30 ml of dry dimethylformamide, and the solution was allowed to stand overnight at room temperature. After removal of any insoluble materials, the filtrate was evaporated under reduced pressure. 50 ml of ethyl acetate and 100 ml of 0.1N hydrochloric acid were added to the residue. The aqueous layer was washed with ethyl acetate and evaporated to obtain 5.4 g of 8'-quinolyl trans-4-guanidinomethylcyclohexanecarboxylate hydrochloride as slightly green syrup.

EXAMPLE 27

3'-Flavonyl trans-4-guanidinomethylcyclohexanecarboxylate hydrochloride

A mixture of 9.89 g of trans-4-guanidinomethylcyclohexanecarboxylic acid hydrochloride, 10.1 g of 3-hydroxyflavon and 8.66 g of dicyclohexylcarbodiimide was added to 100 ml of dry pyridine, and the resulting mixture was stirred at room temperature for 16 hours. The reaction mixture was filtered to remove any insoluble materials which were washed with pyridine. The filtrate and the washing were combined and evaporated. 0.1N hydrochloric acid was added to the residue, and the mixture was washed with ethyl acetate. The aqueous layer was concentrated to 30 ml and allowed to stand overnight in a refrigerator to obtain 1 g of 3'-flavonyl trans-4-guanidinomethylcyclohexanecarboxylate hydrochloride as colorless needles having a melting point of 201°–203° C.

IR $\nu_{max}^{KBr}$ cm$^{-1}$: 1768 (C=O).

NMR(CD$_3$OD) δ: 1.98–2.66 (10H, m, cyclohexane protons), 3.06 (2H, d, J=6.0 Hz, C$\underline{H}_2$N), 7.22–8.14 (9H, m, aromatic protons).

EXAMPLE 28

4'-Chloronaphthyl trans-4-guanidinomethylcyclohexanecarboxylate hydrochloride A mixture of 3.3 g of trans-4-guanidinomethylcyclohexanecarboxylic acid hydrochloride, 2.5 g of 4-chloronaphthol and 3.2 g of dicyclohexylcarbodiimide was suspended in 42 ml of dry pyridine, and the suspension was stirred at room temperature for 48 hours. After removal of any insoluble materials, the filtrate was concentrated. 42 ml of 0.1N hydrochloric acid was added to the residue, and the mixture was stirred at room temperature for 30 minutes to give crystals. The crystals were washed with ether and recrystalized from ethanol-ether to obtain 4.2 g (yield: 75.7%) of 4'-chloronaphthyl trans-4-guanidinomethylcyclohexanecarboxylate hydrochloride having a melting point of 200°–201.5° C.

IR $\nu_{max}^{KBr}$ cm$^{-1}$: 1755 (C=O).

EXAMPLE 29

2'-(1'-Nitro)naphthyl trans-4-guanidinomethylcyclohexanecarboxylate hydrochloride A mixture of 10.0 g of trans-4-guanidinomethylcyclohexanecarboxylic acid hydrochloride, 8.0 g of 1-nitro-2-naphthol and 8.75 g of dicyclohexylcarbodiimide was suspended in 100 ml of dry pyridine, and the suspension was stirred at room temperature for 15 hours. After removal of any insoluble materials, the filtrate was concentrated under reduced pressure. 200 ml of hydrochloric acid was added to the residue, and the mixture was stirred for 1 hour to give crystals. The crystals were washed with water and then with ethyl acetate, and thereafter dried. The crystals obtained were suspended in water-chloroform, and the suspension was stirred overnight to give crystals. These crystals were washed with water and then with ethyl acetate, and dried to obtain 14 g of 2'-(1'-nitro)naphthyl trans-4-guanidinomethylcyclohexanecarboxylate hydrochloride having a melting point of 159°–160.5° C.

IR $\nu_{max}^{KBr}$ cm$^{-1}$: 1762 (C=O).

NMR(DMSO-d$_6$) δ: 0.96–2.08 (10H, m, cyclohexane protons), 3.08 (2H, d, C$\underline{H}_2$N), 7.10–7.78 (6H, m, aromatic protons).

The invention now being fully described, it will be apparent to one of ordinary skill in the art that many changes and modifications can be made thereto without departing from the spirit or scope of the invention as set forth herein.

What is claimed is:
1. 4'-t-Butylphenyl trans-4-guanidinomethylcyclohexanecarboxylate hydrochloride.
2. 4'-t-Butylphenyl trans-4-guanidinomethylcyclohexanecarboxylate and pharmaceutically acceptable salts thereof.

* * * * *

UNITED STATES PATENT AND TRADEMARK OFFICE
CERTIFICATE OF CORRECTION

PATENT NO. : 4,465,851
DATED : August 14, 1984
INVENTOR(S) : Muramatsu et al.

It is certified that error appears in the above-identified patent and that said Letters Patent is hereby corrected as shown below:

Title page, item [75] Inventors: add the following;
--Yoshio Kikawa, Saitama-ken, Japan,
  Kaname Kondo, Tokyo, Japan--.

Signed and Sealed this

First Day of June, 1993

Attest:

MICHAEL K. KIRK

*Attesting Officer*   *Acting Commissioner of Patents and Trademarks*